US010821191B2

(12) United States Patent
Voortman et al.

(10) Patent No.: US 10,821,191 B2
(45) Date of Patent: Nov. 3, 2020

(54) SYD985 TREATMENT OF T-DM1 REFRACTORY CANCER PATIENTS

(71) Applicant: Byondis B.V., Nijmegen (NL)

(72) Inventors: Gerrit Voortman, Nijmegen (NL); Norbert Peter Koper, Nijmegen (NL)

(73) Assignee: Byondis B.V., Nijmegen (NL)

( * ) Notice: Subject to any disclaimer, the term of this patent is extended or adjusted under 35 U.S.C. 154(b) by 135 days.

(21) Appl. No.: 15/762,171

(22) PCT Filed: Sep. 21, 2016

(86) PCT No.: PCT/EP2016/072464
§ 371 (c)(1),
(2) Date: Mar. 22, 2018

(87) PCT Pub. No.: WO2017/050846
PCT Pub. Date: Mar. 30, 2017

(65) Prior Publication Data
US 2018/0280533 A1    Oct. 4, 2018

(30) Foreign Application Priority Data

Sep. 22, 2015 (EP) .................................... 15186258
Mar. 4, 2016 (EP) .................................... 16158710
May 13, 2016 (EP) .................................... 16169699

(51) Int. Cl.
*A61K 47/68* (2017.01)
*A61P 35/04* (2006.01)
*C07K 16/32* (2006.01)

(52) U.S. Cl.
CPC ...... *A61K 47/6855* (2017.08); *A61K 47/6803* (2017.08); *A61K 47/6889* (2017.08); *A61P 35/04* (2018.01); *C07K 16/32* (2013.01)

(58) Field of Classification Search
None
See application file for complete search history.

(56) References Cited

FOREIGN PATENT DOCUMENTS

WO    WO2015/104385    10/2011
WO    WO2011/133039    7/2015

OTHER PUBLICATIONS

Dokter et al. ("Dokter II", Mol. Cancer Ther., 2014, 13, 2618-2629) (Year: 2014).*
Dokter, Willem H. A. et el., "Abstract 2652: In vitro and in vivo antitumor activity of SYD985, a novel HR2-targeting ADC: a comparison with T-DM1 Cancer Research" Cancer Research, Oct. 1, 2014, entire document.
Van Der Lee, M.M.C. et al., "The Preclinical Profile of the Duocarmycin-Based HER2-Targeting ADC SYD985 Predicts for Clinical Benefit in Low HER2-Expressing Breast Cancers" Molecular Cancer Therapeutics, vol. 14, No. 3, Jan. 14, 2015, pp. 692-703.

* cited by examiner

*Primary Examiner* — Karl J Puttlitz
(74) *Attorney, Agent, or Firm* — Buscher Patent PLLC

(57) ABSTRACT

The present invention relates to the duocarmycin-containing antibody-drug conjugate (ADC) trastuzumab vc-seco-DUBA (SYD985) for use in the treatment of trastuzumab emtansine (T-DM1) refractory HER2 IHC 3+ or HER2 IHC 2+/FISH positive cancer patients, particularly T-DM1 refractory breast cancer patients.

14 Claims, 1 Drawing Sheet

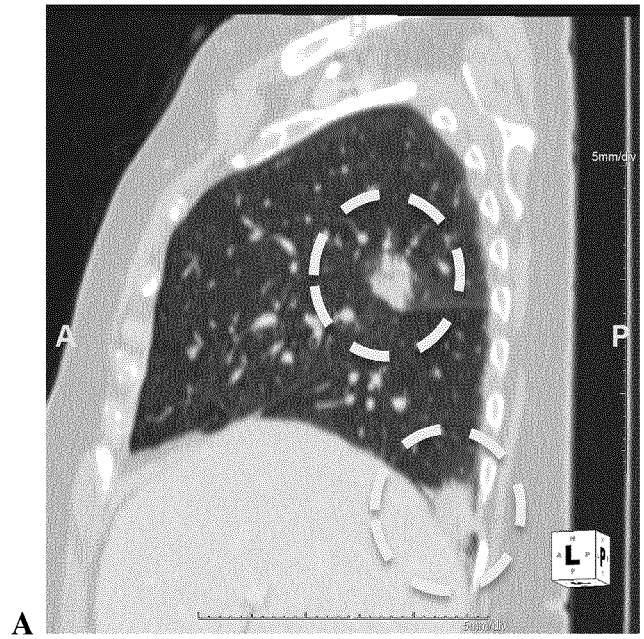
A
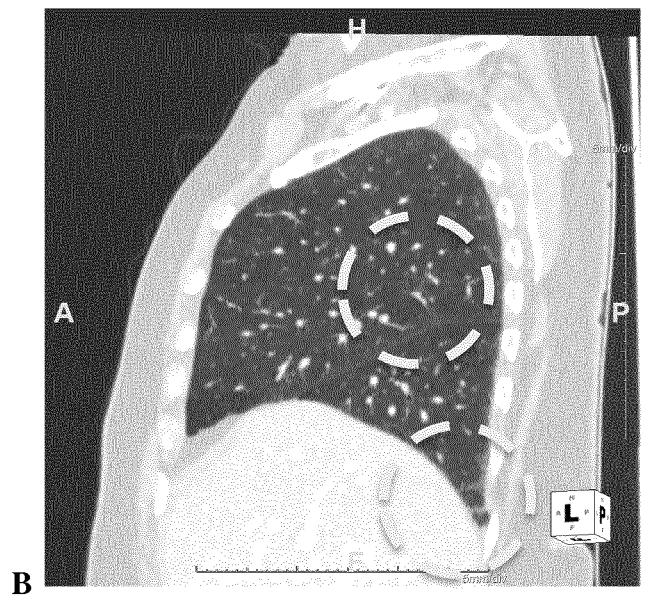
B

SYD985 TREATMENT OF T-DM1 REFRACTORY CANCER PATIENTS

FIELD OF THE INVENTION

The present invention relates to the treatment of trastuzumab emtansine (T-DM1) refractory cancer patients, particularly T-DM1 refractory breast cancer patients.

BACKGROUND OF THE PRESENT INVENTION

Antibodies have been conjugated to a variety of cytotoxic drugs, including small molecules that bind DNA (e.g. anthracyclines), alkylate or crosslink DNA (e.g. duocarmycins and pyrrolobenzodiazepine dimers, respectively), cause DNA strand breaks (e.g. calicheamicins) or disrupt microtubules (e.g. maytansinoids, auristatins, and tubulysins). These combined molecules are referred to as antibody-drug conjugates (ADCs).

Duocarmycins, first isolated from a culture broth of *Streptomyces* species, are members of a family of antitumor antibiotics that include duocarmycin A, duocarmycin SA, and CC-1065. Duocarmycins bind to the minor groove of DNA and subsequently cause irreversible alkylation of DNA. This disrupts the nucleic acid architecture, which eventually leads to tumor cell death.

WO 2011/133039 discloses a series of analogues of the DNA-alkylating agent CC-1065 and HER2-targeting ADCs thereof. In Example 15, a number of trastuzumab-duocarmycin conjugates were tested against N87 (i.e., HER2 IHC (immunohistochemistry) 3+ gastric tumor) xenografts in nude mice. The results are shown in FIGS. 4A, 4B and 4C of WO 2011/133039. After treatment with a single dose of 12 mg/kg i.v., all six ADCs reduced the tumor volume and improved survival compared to the antibody trastuzumab itself and control vehicle, without affecting body weight.

M.M.C. van der Lee et al. in Mot. Cancer Ther. 2015, 14(3), 692-703 disclose the preclinical profile of the duocarmycin-based HER2-targeting ADC SYD985. In vivo antitumor studies in breast cancer patient-derived tumor xenograft (PDX) models showed that SYD985 is very active in HER2 3+, 2+, and 1+ models, whereas T-DM1 only showed significant antitumor activity in HER2 3+ breast cancer PDX models. The authors conclude that these properties of SYD985 may enable expansion of the target population to patients who have low HER2-expressing breast cancer, a patient population with high, still unmet medical need.

WO 2015/104385 discloses duocarmycin-containing ADCs for use in the treatment of human solid tumors and haematological malignancies expressing HER2, in particular for use in the treatment of human solid tumors with HER2 IHC 2+ or 1+ and HER2 FISH (fluorescence in situ hybridization) negative tissue status. In FIGS. 1 to 11, the antitumor activity of SYD985 is compared to T-DM1 in a number of breast cancer, gastric cancer, bladder cancer and ovarian cancer PDX animal models. WO 2015/104385 describes SYD985 which has an average drug-to-antibody ratio (DAR) of from 2.6 to 2.9.

Herceptin™ (trastuzumab), a recombinant humanized IgG1 monoclonal antibody against HER2, was approved in the US by the FDA in 1998 for the treatment of metastatic HER2 over-expressing breast cancer and gastric cancer, i.e., HER2 IHC 3+ or HER2 IHC 2+/FISH positive and in 2006 for adjuvant treatment of HER2 over-expressing breast cancer. The drug was approved in Europe by the EMA in 2000.

Clinical studies in patients with metastatic breast cancer have demonstrated that there is only clinically relevant efficacy of trastuzumab treatment if the patient has a tumor with HER2 IHC over-expression or FISH positive gene amplification, i.e., HER2 IHC 3+ or HER2 IHC 2+/FISH positive. For this reason, current HER2 testing algorithms are aimed at identifying those patients most likely to achieve a significant benefit from HER2 targeting therapy.

Kadcyla™ (trastuzumab emtansine, ado-trastuzumab emtansine or T-DM1) is an ADC in which trastuzumab is conjugated to the cytotoxic anti-tubulin agent emtansine (DM1). T-DM1 has antitumor activity in tumor xenograft models that are not responding to therapy with trastuzumab as single agent. In the Phase III EMILIA trial, patients with HER2 positive locally advanced or metastatic breast cancer, previously treated with trastuzumab and a taxane, were randomly assigned to receive T-DM1 or lapatinib plus capecitabine. T-DM1 treatment effectuated significantly longer progression-free and overall survival time than treatment with lapatinib plus capecitabine.

Kadcyla™ was approved in the US by the FDA in 2013 for the treatment of patients with HER2-positive metastatic breast cancer who received prior treatment with trastuzumab and a taxane. The drug was also approved in 2013 in Japan by the MHLW (Ministry of Health, Labour and Welfare) and in Europe by the EMA. The currently approved regimen comprises a dosage of 3.6 mg/kg body weight i.v. every 3 weeks.

In 2015, the Phase II/III GATSBY trial, in which a dosage of 2.4 mg/kg T-DM1 once a week was compared with a 3-weekly dosage of 3.6 mg/kg T-DM1 or taxane regimen for second line treatment of patients with advanced gastric cancer did not meet its primary endpoint (3 years overall survival).

The suitability of the same 3-weekly dosage regimen of 3.6 mg/kg T-DM1 for the treatment of non-small cell lung cancer (NSCLC) is currently being evaluated in a Phase II study.

Despite the improvement over trastuzumab for the treatment of HER2-positive (metastatic) breast cancer by the introduction of T-DM1 in clinical practice, T-DM1 can cause severe problems of heart, liver and lung with additional possible serious infusion related reactions, bleeding, low platelet count, nerve damage and skin reactions around the infusion site. Consequently, treatment with T-DM1 may have to be discontinued because of (unacceptable) toxicity.

Furthermore, cancer patients, particularly (metastatic) breast cancer patients, may become refractory to T-DM1 treatment, meaning that after an initial positive response to T-DM1 such treatment is discontinued because of disease progression. Hence, there is a high medical need for new HER2-targeted therapies for the treatment of T-DM1 refractory cancer patients.

SUMMARY OF THE INVENTION

Surprisingly, it was found that it is possible to treat patients that do no longer respond to trastuzumab conjugated to a DM1 payload, with trastuzumab conjugated to a duocarmycin payload, in spite of the fact that both conjugates use the same antibody for delivering the payload.

In one aspect, the invention relates to a compound of formula (I) for use in the treatment of T-DM1 refractory cancer patients.

In another aspect, the invention relates to a pharmaceutical composition comprising the compound of formula (I) and one or more pharmaceutically acceptable excipients for use in the treatment of T-DM1 refractory cancer patients.

In yet another aspect, the invention relates to a method of treating a T-DM1 refractory cancer patient, particularly a T-DM1 refractory breast cancer patient, comprising administering to the patient a therapeutically effective amount of a compound of formula (I).

In yet another aspect, the invention relates to a combination therapy of a compound of formula (I) with an immune checkpoint inhibitor.

In yet another aspect, the invention relates to a method of treating a T-DM1 refractory cancer patient, particularly a T-DM1 refractory breast cancer patient, comprising administering to the patient a therapeutically effective amount of a compound of formula (I), followed by administering a therapeutically effective amount of an immune checkpoint inhibitor.

Other aspects and advantages of the invention will be readily apparent from the following detailed description of the invention. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWING

FIG. 1 shows computed tomography (CT) scans (A: baseline, B: after 6 i.v. infusions of 1.2 mg/kg SYD985 every 3 weeks) of the lung of a 59-year-old. HER2-positive breast cancer patient with lung and bone metastases.

DETAILED DESCRIPTION OF THE INVENTION

The present invention relates to trastuzumab vc-seco-DUBA (SYD985) for use in the treatment of trastuzumab emtansine (T-DM1) refractory cancer patients, particularly T-DM1 refractory breast cancer patients.

The present invention provides a compound of formula (I) for use in the treatment of T-DM1 refractory cancer patients, wherein 2.6-2.9 represent an average DAR for the compound. The compound of formula (I) is referred to as SYD985 in the present specification. In one embodiment, SYD985 has an average DAR of from 2.7 to 2.9. In specific embodiments of the present invention, SYD985 has an average DAR of about 2.7, about 2.8, or about 2.9. In one particular embodiment, SYD985 has an average DAR of about 2.8.

Unexpectedly, the present inventors have found that HER2 IHC 3+ or HER2 IHC 2+/FISH positive cancer patients, particularly HER2 IHC 3+ or HER2 IHC 2+/FISH positive breast cancer patients, who are refractory to i) T-DM1 alone, ii) trastuzumab and T-DM1, or iii) trastuzumab, lapatinib and T-DM1, can still be successfully treated with SYD985 in spite of the fact that SYD985 uses trastuzumab to deliver the duocarmycin payload. Hence, a new treatment option has become available for patients that no longer respond to treatment with currently available HER2-targeted therapies.

In the context of the present invention, the term "refractory" means "acquired resistance to the specified drug(s) (e.g. T-DM1)", as opposed to "de novo resistance to the specified drug(s) (e.g. T-DM1)", meaning that the patient initially showed a "partial response" or "stable disease" after treatment with the specified drug(s) (e.g. T-DM1), but that treatment was discontinued after at least 2 treatment cycles because of disease progression.

In one embodiment of the present invention, the cancer patient is refractory to at least one further anti-HER2 agent in addition to T-DM1, such as trastuzumab, pertuzumab, or lapatinib, or to another tyrosine kinase inhibitor such as gefitinib, erlotinib, pazopanib, crizotinib, or afatinib. In another embodiment, the cancer patient is refractory to both trastuzumab and T-DM1 or to all of trastuzumab, lapatinib and T-DM1.

In another embodiment of the present invention, the cancer patient is a HER2 IHC 3+ or HER2 IHC 2+/FISH positive breast cancer patient, a HER2 IHC 3+ or HER2 IHC 2+/FISH positive gastric cancer patient, or a HER2 IHC 3+ or HER2 IHC 2+/FISH positive lung cancer patient, particularly a HER2 IHC 3+ or HER2 IHC 2+/FISH positive breast cancer patient, more particularly a HER2 IHC 3+ or HER2 IHC 2+/FISH positive metastatic breast cancer patient.

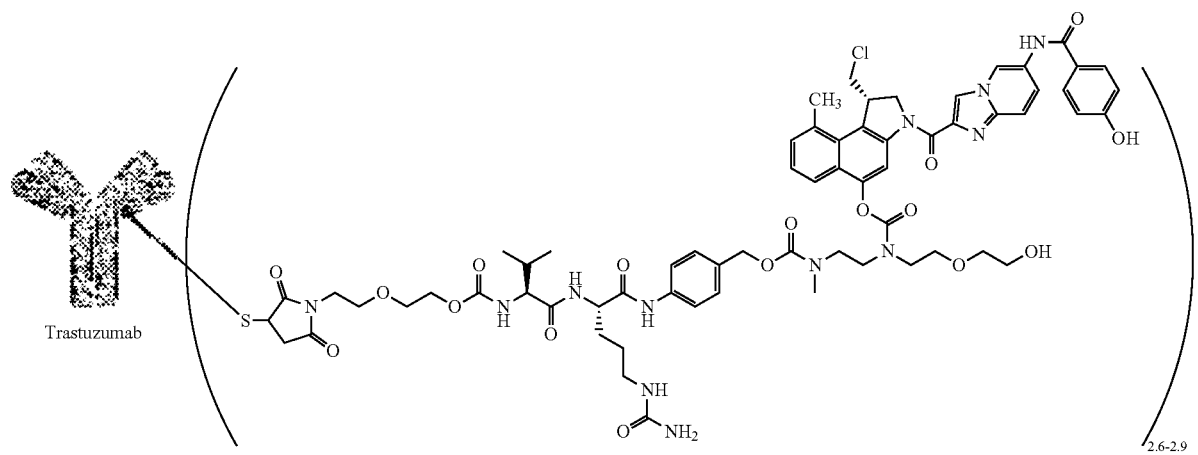

The present invention further relates to a method of treating a T-DM1 refractory HER2 IHC 3+ or HER2 IHC 2+/FISH positive cancer patient, particularly a T-DM1 refractory HER2 IHC 3+ or HER2 IHC 2+/FISH positive breast cancer patient, a HER2 IHC 3+ or HER2 IHC 2+/FISH positive gastric cancer patient, or a HER2 IHC 3+ or HER2 IHC 2+/FISH positive lung cancer patient, more particularly a T-DM1 refractory HER2 IHC 3+ or HER2 IHC 2+/FISH positive breast cancer patient, most particularly a HER2 IHC 3+ or HER2 IHC 2+/FISH positive metastatic breast cancer patient, comprising administering to the patient a therapeutically effective amount of a compound of formula (I).

In one embodiment of the method of treating a T-DM1 refractory HER2 IHC 3+ or HER2 IHC 2+/FISH positive cancer patient, the average DAR for the compound is about 2.8.

In another embodiment of the method of treating a T-DM1 refractory HER2 IHC 3+ or HER2 IHC 2+/FISH positive cancer patient, the patient is refractory to at least one further anti-HER2 agent in addition to T-DM1, such as trastuzumab, pertuzumab, or lapatinib, or to another tyrosine kinase inhibitor such as gefitinib, erlotinib, pazopanib, crizotinib, or afatinib.

In one embodiment of the method of treating a T-DM1 refractory HER2 IHC 3+ or HER2 IHC 2+/FISH positive cancer patient, said T-DM1 refractory cancer is HER2 IHC 3+ or HER2 IHC 2+/FISH positive breast cancer, more particularly said T-DM1 refractory cancer is HER2 IHC 3+ or HER2 IHC 2+/FISH positive metastatic breast cancer.

In one embodiment of the method of treating a T-DM1 refractory HER2 IHC 3+ or HER2 IHC 2+/FISH positive cancer patient, the patient is a human.

In another embodiment of the method of treating a T-DM1 refractory HER2 IHC 3+ or HER2 IHC 2+/FISH positive breast cancer patient, the average DAR for the compound is about 2.8.

In another embodiment of the method of treating a T-DM1 refractory HER2 IHC 3+ or HER2 IHC 2+/FISH positive breast cancer patient, the patient is refractory to both trastuzumab and T-DM1 or to all of trastuzumab, lapatinib and T-DM1.

The present invention still further relates to a combination of an ADC compound of formula (I) and an immune checkpoint inhibitor (ICI) for use in the treatment of T-DM1 refractory HER2 IHC 3+ or HER2 IHC 2+/FISH positive cancer patients as described hereinabove.

One of the basic defence mechanisms against cancer development are the innate and adaptive immune systems. Tumor cell chromosomal instability and mutational load are thought to be causative in the increased expression of tumor-associated neo-antigens that can trigger a tumor-specific immune response. Unfortunately, expression of 'don't eat me' signals in the tumor, such as CTLA-4 and PD-1 associated signalling molecules, can effectively nullify an anti-tumor immune response. CTLA-4/PD-1/PD-L1 blocking antibodies, known as immune checkpoint inhibitors (ICIs), are capable of reactivating such a silent antitumor immune response in a subpopulation of cancer patients and have led to their approval as a monotherapy for the treatment of cancer i.e. Yervoy™ (ipilimumab), Keytruda™ (pembrolizumab), Opdivo™ (nivolumab) and Tecentriq™ (atezolizumab).

DNA-damaging agents, when not immediately killing the tumor cell, are expected to increase neo-antigen load and thereby elicit novel antitumor immune responses. Various anthracyclines, cyclophosphamide, oxaliplatin, and ionizing radiation have been shown to induce immunogenic cell death (ICD), a non-conventional type of apoptosis that is associated with the activation of an adaptive immune response against dead cell-associated antigens. In addition, certain tubulin-interacting chemotherapeutics (docetaxel, MMAE, DM1) have been shown to induce dendritic cell (DC) maturation thereby triggering subsequent immune responses.

Combination therapies of DNA-damaging agents or therapeutics that trigger ICD or DC maturation with an ICI are expected to lead to synergy in terms of antitumor efficacy. Combination therapies of an ADC with an ICI are the subject of a number of ongoing clinical trials.

Examples of suitable ICIs for use in accordance with the present invention include antibodies against CTLA-4, such as ipilimumab (Yervoy™) and tremelimumab, antibodies against PD-1 such as nivolumab (Opdivo™) and pembrolizumab (Keytruda™), antibodies against PD-L1 such as atezolizumab (Tecentriq™), avelumab and RG7446, and antibodies such as elotuzumab. The ADC compound of formula (I) and the ICI either can be co-administered or administered sequentially. In one embodiment in accordance with the present invention, the ADC compound of formula (I) is administered first, followed by administration of the ICI (e.g. to reactivate the patient's immune system).

The present invention still further relates to a pharmaceutical composition comprising a compound of formula (I) and one or more pharmaceutically acceptable excipients for use in the treatment of T-DM1 refractory HER2 IHC 3+ or HER2 IHC 2+/FISH positive cancer patients.

Typical pharmaceutical formulations of therapeutic proteins such as monoclonal antibodies and ADCs take the form of lyophilized powders or cakes, which require (aqueous) dissolution (i.e., reconstitution) before intravenous infusion, or frozen (aqueous) solutions, which require thawing before use. Particularly, in accordance with the present invention the pharmaceutical composition is provided in the form of a lyophilized cake.

Suitable pharmaceutically acceptable excipients for inclusion into the pharmaceutical composition (before freeze-drying) in accordance with the present invention include buffer solutions (e.g. citrate, histidine or succinate containing salts in water), lyoprotectants (e.g. sucrose or trehalose), tonicity modifiers (e.g. sodium chloride), surfactants (e.g. polysorbate), and bulking agents (e.g. mannitol or glycine). Excipients used for freeze-dried protein formulations are selected for their ability to prevent protein denaturation during the freeze-drying process as well as during storage.

In one embodiment in accordance with the present invention, a lyophilized powder pharmaceutical composition is provided wherein, when reconstituted with 8 ml water (e.g. bacteriostatic or sterile water-for-injection), SYD985 is present in an amount of about 10 mg/ml, the concentration of histidine is about 5 mM, the amount of polysorbate 20 is about 0.01% (m/v), and the pH is about 5.7.

A therapeutically effective amount (dose) of SYD985 for use in accordance with the present invention lies in the range of from about 0.6 mg/kg to about 3 mg/kg of patient body weight, particularly in the range of from about 0.9 mg/kg to about 2.4 mg/kg, more particularly in the range of from about 0.9 mg/kg to about 2.1 mg/kg, even more particularly in the range of from about 1.2 mg/kg to about 2.1 mg/kg, and most particularly in the range of from about 1.2 mg/kg to about 1.8 mg/kg of patient body weight per administration. Administration is typically done via intravenous (i.v.) infusion.

In accordance with the present invention, SYD985 is administered every week, every 2 weeks or every 3 weeks, preferably every 3 weeks, until disease progression or development of unacceptable toxicity. In a two-part first-in-human phase I study, SYD985 was shown to be well-tolerated up to a dose of 1.8 mg/kg patient body weight per i.v. administration every 3 weeks.

Alternative treatment (dose) regimens—including those suitable for combination therapy of an ADC compound of formula (I) with an ICI such as ipilimumab, nivolumab, pembrolizumab or atezolizumab—may be used depending upon the severity of the disease, the age of the patient, and such other factors as would be considered appropriate by the treating physician. For example, a treatment regimen in which a particular dose of SYD985 is given every 3 weeks for a number of cycles followed by a lower dose every 3 weeks (e.g. 1.2 mg/kg every 3 weeks for 4 cycles followed by 0.9 mg/kg every 3 weeks) or a treatment regimen in which a particular dose of SYD985 is given every 3 weeks for a number of cycles followed by the same dose every 6 weeks (e.g. 1.2 mg/kg every 3 weeks for 4 cycles followed by 1.2 mg/kg every 6 weeks).

In one embodiment of the present invention, the patient is treated, preferably every 3 weeks, with a dose of SYD985 in the range of from about 0.9 mg/kg to about 2.1 mg/kg, particularly in the range of from about 1.2 mg/kg to about 2.1 mg/kg, more particularly in the range of from about 1.2 mg/kg to about 1.8 mg/kg of patient body weight per i.v. administration.

In another embodiment of the present invention, the patient is treated, preferably every 3 weeks, with a dose of SYD985 in the range of from about 0.6 mg/kg to about 2.1 mg/kg, particularly in the range of from about 0.9 mg/kg to about 1.8 mg/kg, more particularly in the range of from about 0.9 mg/kg to about 1.5 mg/kg of patient body weight per i.v. administration.

In another embodiment in accordance with the present invention, the patient is treated, preferably every 3 weeks, with a dose of SYD985 of about 0.9 mg/kg, about 1.2 mg/kg, about 1.5 mg/kg, about 1.8 mg/kg, or about 2.1 mg/kg of patient body weight per i.v. administration.

In yet another embodiment in accordance with the present invention, the patient is treated, preferably every 3 weeks, with a dose of SYD985 of about 1.2 mg/kg of patient body weight per i.v. administration.

In one embodiment of the method of treating a T-DM1 refractory HER2 IHC 3+ or HER2 IHC 2+/FISH positive breast cancer patient, the compound is administered at a dose of from about 0.9 mg/kg to about 2.1 mg/kg of patient body weight per i.v. administration every 3 weeks, preferably of from about 1.2 to about 1.8 mg/kg of patient body weight per intravenous administration every 3 weeks.

In another embodiment of the method of treating a T-DM1 refractory HER2 IHC 3+ or HER2 IHC 2+/FISH positive breast cancer patient, the dose is about 0.9 mg/kg of patient body weight per i.v. administration every 3 weeks.

In yet another embodiment of the method of treating a T-DM1 refractory HER2 IHC 3+ or HER2 IHC 2+/FISH positive breast cancer patient, the dose is about 1.2 mg/kg of patient body weight per i.v. administration every 3 weeks.

In yet another embodiment of the method of treating a T-DM1 refractory HER2 IHC 3+ or HER2 IHC 2+/FISH positive breast cancer patient, the dose is about 1.5 mg/kg of patient body weight per i.v. administration every 3 weeks.

In yet another embodiment of the method of treating a T-DM1 refractory HER2 IHC 3+ or HER2 IHC 2+/FISH positive breast cancer patient, the dose is about 1.8 mg/kg of patient body weight per i.v. administration every 3 weeks.

In yet another embodiment of the method of treating a T-DM1 refractory HER2 IHC 3+ or HER2 IHC 2+/FISH positive breast cancer patient, the dose is about 2.1 mg/kg of patient body weight per i.v. administration every 3 weeks.

In another embodiment in accordance with the present invention, treatment with an ADC compound of formula (I), preferably SYD985 with an average DAR of about 2.8, is followed by treatment with an ICI, preferably ipilimumab (Yervoy™), nivolumab (Opdivo™), pembrolizumab (Keytruda™) or atezolizumab (Tecentriq™).

EXAMPLES

First-in-Human Clinical Study

A two-part first-in-human phase I study (with expanded cohorts) with the antibody-drug conjugate SYD985 (trastuzumab vc-seco-DUBA), having an average DAR of about 2.8, was started to evaluate the safety, pharmacokinetics and efficacy in patients with locally advanced or metastatic solid tumors (i.e., NCT02277717). Part I is the dose-escalation part in which a low dose of SYD985 was given to three or six cancer patients (females or males having solid tumors of any origin). If it were well tolerated, a higher dose of SYD985 was given to three or six other cancer patients. This continued until it was not safe anymore to increase the dose further. Any dose level could be extended with additional patients. In part II of the study, several groups of patients with a specific type of cancer (including breast and gastric tumors) will receive the SYD985 dose selected for further development. All patients from both parts of the study will receive SYD985 (i.v.) infusions until the cancer progresses or unacceptable toxicity develops.

Results

SYD985 was well-tolerated up to a dose of 1.8 mg/kg patient body weight per i.v. administration every 3 weeks. Promising efficacy was observed at doses of >1.2 mg/kg patient body weight. Partial responses (according to RECIST 1.1; see E. A. Eisenhower et al. in Eur. J. Cancer 45 (2009) 228-247) were observed in five HER2 IHC 3+ or HER2 IHC 2+/FISH positive breast cancer patients refractory to both trastuzumab and T-DM1.

Response Criteria for Target Lesions

Complete response (CR): Disappearance of all target lesions. Any pathological lymph nodes (whether target or non-target) must have reduction in short axis to <10 mm.

Partial response (PR): At least a 30% decrease in the sum of diameters of target lesions, taking as reference the baseline sum diameters.

Progressive disease (PD): At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression.

Stable disease (SD): Neither sufficient shrinkage to qualify for PR nor sufficient increase to qualify for PD, taking as reference the smallest sum diameters while on study.

Representative data are summarized in Table 1 below.

TABLE 1

Efficacy of SYD985 in HER2-positive, T-DM1 refractory[1] breast cancer patients

| Patient | Dosage | Duration of treatment | Best response | Max. % change from baseline |
|---|---|---|---|---|
| 1[2] | 1.2 mg/kg every 3 weeks | 10 months | PR | −100% |
| 2[3] | 1.2 mg/kg every 3 weeks | 7 months | PR | −75% |
| 3[3] | 1.8 mg/kg every 3 weeks | 4 months | PR | −63% |
| 4[3] | 1.8 mg/kg every 3 weeks | 8 months | PR | −54% |
| 5[3] | 2.4 mg/kg every 3 weeks | 2 months | PR | −30% |

[1]T-DM1 was discontinued in all patients because of progressive disease
[2]Patient also received prior trastuzumab
[3]Patient also received prior trastuzumab and lapatinib FIG. 1 shows computed tomography (CT) scans (A: baseline, B: after 6 i.v. infusions of 1.2 mg/kg SYD985 every 3 weeks) of the lung of a 59-year-old HER2-positive breast cancer patient with lung and bone metastases, i.e., patient 1 in Table 1 above. This patient was refractory to trastuzumab and T-DM1. PR was achieved after 2 i.v. infusions of 1.2 mg/kg SYD985 every 3 weeks, reaching complete response (CR) in lung target lesions after 6 i.v. infusions of 1.2 mg/kg SYD985 every 3 weeks.

Most noticeably, very high response rates and durable responses were observed in patients whose cancers were refractory to HER2-targeted agents, including trastuzumab and T-DM1, following treatment with SYD985 at doses from 1.2 mg/kg onwards, particularly at a dose of 1.2 mg/kg every three weeks.

Part II of the Phase I Study (SYD985.001 Trial)

In part II of the phase I study an expanded (first) cohort of 48 patients with (end-stage) HER2-positive (i.e., IHC HER2 3+ or IHC HER2 2+/FISH positive) metastatic breast cancer are treated with SYD985 at a starting dose of 1.2 mg/kg in the following three dose regimens: i) 1.2 mg/kg every 3 weeks, ii) 1.2 mg/kg every 3 weeks for 4 cycles followed by 0.9 mg/kg every 3 weeks, and iii) 1.2 mg/kg every 3 weeks for 4 cycles followed by 1.2 mg/kg every 6 weeks.

Part II was started in April 2016. Data from this cohort will enable to design a first pivotal trial with SYD985.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method of treating a trastuzumab emtansine refractory tumor, which comprises administering to a trastuzumab emtansine refractory HER2 IHC 3+ or HER2 IHC 2+/FISH positive cancer patient an effective amount of a compound of formula (I)

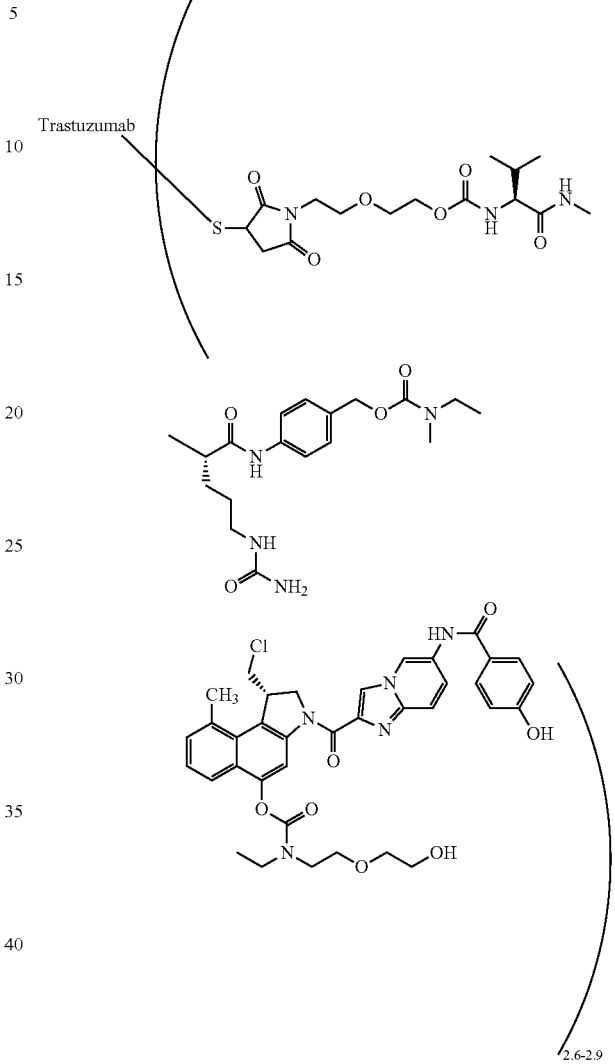

wherein 2.6-2.9 represent an average DAR for the compound.

2. The method according to claim 1, wherein the average DAR for the compound is about 2.8.

3. The method according to claim 1, wherein the patient is refractory to both trastuzumab and trastuzumab emtansine.

4. The method according to claim 1, wherein the patient is refractory to all of trastuzumab, lapatinib and trastuzumab emtansine.

5. The method according to claim 1, wherein the patient is a breast cancer patient.

6. The method according to claim 1, wherein said compound is administered at a dose of from about 0.9 mg/kg to about 2.1 mg/kg of patient body weight by intravenous administration.

7. The method according to claim 6, wherein the dose is about 0.9 mg/kg, about 1.2 mg/kg, about 1.5 mg/kg, about 1.8 mg/kg, or about 2.1 mg/kg of patient body weight.

8. The method according to claim 6, wherein the average DAR for the compound is about 2.8.

9. The method according to claim 6, wherein said dose is administered every 3 weeks.

10. The method according to claim 6, wherein the patient is a breast cancer patient.

11. The method according to claim 6, wherein said dose is about 1.2 to about 1.8 mg/kg of patient body weight.

12. The method according to claim 11, wherein said dose is about 1.2 mg/kg of patient body weight.

13. The method according to claim 12, wherein said dose is administered every 3 weeks.

14. The method according to claim 13, wherein the patient is a breast cancer patient.

* * * * *